United States Patent
Mazaheripour et al.

(10) Patent No.: US 12,130,326 B2
(45) Date of Patent: Oct. 29, 2024

(54) IN VITRO NEURAL IMPLANT TESTER WITH HARDWARE-IN-THE-LOOP SIMULATION

(71) Applicant: Neuralink Corp., Fremont, CA (US)

(72) Inventors: Amir Mazaheripour, Emeryville, CA (US); Joshua S. Hess, Dublin, CA (US); Andrew D. Wong, San Francisco, CA (US); Amir M. Foudeh, San Francisco, CA (US); Ava S. K. Greenwood, San Jose, CA (US); Alan R. Mardinly, Oakland, CA (US); Alejandro J. Tenorio, San Mateo, CA (US); Ian C. C. Switzer, Oakland, CA (US)

(73) Assignee: Neuralink Corp., Fremont, CA (US)

( * ) Notice: Subject to any disclaimer, the term of this patent is extended or adjusted under 35 U.S.C. 154(b) by 470 days.

(21) Appl. No.: 17/524,545

(22) Filed: Nov. 11, 2021

(65) Prior Publication Data

US 2023/0147266 A1    May 11, 2023

(51) Int. Cl.
| | |
|---|---|
| *G01R 31/28* | (2006.01) |
| *A61N 1/37* | (2006.01) |
| *G01R 31/00* | (2006.01) |
| *G06F 1/18* | (2006.01) |
| *A61B 5/00* | (2006.01) |

(52) U.S. Cl.
CPC ....... *G01R 31/2829* (2013.01); *A61N 1/3704* (2013.01); *G01R 31/002* (2013.01); *G06F 1/182* (2013.01); *A61B 5/0031* (2013.01)

(58) Field of Classification Search
CPC .............. G01R 31/2829; G01R 31/002; A61N 1/3704; A61N 1/08; G06F 1/182; G06F 11/26; A61B 5/0031

See application file for complete search history.

(56) References Cited

U.S. PATENT DOCUMENTS

| | | | |
|---|---|---|---|
| 2006/0249136 A1* | 11/2006 | Reay | F24C 15/327 126/20 |
| 2012/0086449 A1* | 4/2012 | Graesslin | G01R 33/285 324/309 |

OTHER PUBLICATIONS

Takamakov et al., Rapid evaluation of the durability of cortical neural implants using accelerated aging with reactive oxygen species, J. Neural Eng., 2015, 16 pages, vol. 12, IOP Publishing, United Kingdom.

* cited by examiner

*Primary Examiner* — Suman K Nath
(74) *Attorney, Agent, or Firm* — Kilpatrick Townsend & Stockton LLP (57) ABSTRACT

Accelerated testing apparatuses for implants are described, as well as methods for accelerated testing implants. The accelerated testing apparatus includes a cabinet having multiple bays and a vessel insertable and removable from any of the multiple bays. The vessel includes a watertight basin, a radio-frequency (RF) transparent lid configured to mate with the basin, and a plurality of fixtures within the vessel. Each fixture is adapted to anchor a device-under-test while submersed within the vessel. The accelerated testing apparatus also includes a reservoir disposed within the cabinet, a heater connected with the reservoir, a pump configured to circulate liquid between the reservoir and the vessel, an antenna within the cabinet for communication with the device-under-test, and at least one computer server operatively connected with the antenna.

18 Claims, 7 Drawing Sheets

IN VITRO NEURAL IMPLANT TESTER WITH HARDWARE-IN-THE-LOOP SIMULATION

CROSS-REFERENCES TO RELATED APPLICATIONS

NOT APPLICABLE

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Invention

Embodiments of the present invention generally relate to anatomical models for testing that are specially adapted to simulate circulation of bodily fluids. More specifically, embodiments relate to a test rack that can perform accelerated aging tests of many wireless neural implants at once using a shared reservoir of temperature controlled and automatically conditioned synthetic cerebral spinal fluid (CSF).

2. Description of the Related Art

Implantable devices are used for a variety of applications such as cardiac pacemakers, cochlear implants, and recording and stimulating electrical signals in target biological tissue. In many cases, active electronic devices are critical to the functionality of the implantable device. As implantable devices advance, it is increasingly common to have a large number of wires extending from the implantable device. For example, a brain-machine interface includes thousands of wires extending from an implantable device and implanted in a brain. Body environments such as brain tissue, heart tissue, and the like have high humidity and bodily fluids. Implantable devices are generally in an in-vivo environment including high humidity and oxidative inflammatory response that will put stress on sensitive components such as active electronics without proper protection. As a result, implantable devices generally undergo failure analysis to determine an appropriate implantation period for the device.

To generate statistically significant confidence in a projected lifetime of an implanted device, a large number of devices need to be tested. Additionally, in-vivo conditions need to be accurately replicated in the testing environment to determine an accurate projected lifetime. Since implanted devices may take years to fail, it may be time intensive to test a sufficient number of devices to generate the statistically significant confidence.

BRIEF SUMMARY

Neural implants undergo testing and failure analysis prior to in-vivo implantation. An accelerated testing apparatus can mimic in-vivo conditions with factors accelerated so as to cause the devices-under-test to fail realistically, but at an accelerated rate than in-vivo. An accelerated testing system can store, heat, and pump liquid similar to that of cerebral spinal fluid (CSF) to multiple devices-under-test. Each of the devices-under-test can connect to a computer server that receives data about the devices-under-test. The devices-under-test can be stored in fixtures of vessels within a bay of a cabinet. The cabinet may have multiple bays, each of which can hold one or more vessels, such that a large number of devices may be tested simultaneously.

Some embodiments of the present disclosure are related to an accelerated testing apparatus for implants that includes a cabinet having multiple bays, a vessel insertable and removable from any of the multiple bays. The vessel includes a watertight basin, a radio-frequency (RF) transparent lid configured to mate with the basin, and a plurality of fixtures within the vessel. Each fixture is adapted to anchor a device-under-test while submersed within the vessel. The accelerated testing apparatus further includes a reservoir disposed within the cabinet, a heater connected with the reservoir, a pump configured to circulate liquid between the reservoir and the vessel, an antenna within the cabinet for communication with the device-under-test, and at least one computer server operatively connected with the antenna.

The vessel can be a first vessel, and the apparatus can further include other vessels substantially identical to the first vessel. The first and other vessels can be installed in the cabinet and connected to and share common liquid with the reservoir. The at least one computer server can index multiple devices-under-test within the vessels regardless of position within the cabinet and record data from the multiple devices-under-test.

The apparatus can include a peroxide dispenser fluidically connected with the reservoir. The apparatus can also include a peroxide sensor disposed within the reservoir and connected with the at least one computer server. The computer server can command or withhold dispensing of peroxide from the peroxide dispenser based upon measurements from the peroxide sensor.

The fixture can include a first part yoked to a second part so as to permit limited movement between the first and second parts. The first and second parts can be adapted to hold portions of the respective device-under-test that are flexibly interconnected. The second part of the fixture can include a simulated tissue well into which electrodes from the device-under-test can be affixed.

The apparatus can include a controller configured to pulse pressure from the pump in order to induce cyclic mechanical fatigue between the portions of the device-under-test. The computer server can be connected with the controller.

The heater can be an immersion heater. Metal portions along an immersion length of the immersion heater can be coated in polymer. The reservoir can include a chamber that is glass, corrosion-resistant metal, or temperature-stable plastic, which is heated from the outside (i.e. from heating pads, resistive coils, etc.) in order to heat the liquid.

The apparatus can further include a clamp or latch configured to force together the lid and watertight basin to hermetically seal the vessel. The vessel and the reservoir are configured to be pressurized to at least 202,650 pascals (2 atmospheres).

The apparatus can further include a dock for a power transmission coil adjacent to each fixture. The power transmission coil is adapted to power the respective device-under-test.

The apparatus can further include a sensor connected with the reservoir and configured to measure pH, ionic concentration, temperature, or pressure.

The cabinet can be an 18 U-or-greater size server cabinet.

Some embodiments include a method for accelerated testing implants. The method includes inserting multiple devices-under-test into a plurality of fixtures within a vessel having a watertight basin and radio-frequency (RF) transparent lid, mating the lid with the watertight basin to close the vessel, inserting the vessel with the devices-under-test into a cabinet having multiple bays, the vessel being insertable and removable from any of the multiple bays, connecting the vessel to a reservoir disposed within the cabinet, heating and pumping liquid from the reservoir through the vessel, and wirelessly recording data from the multiple devices under test to at least one computer server in the cabinet.

The vessel can be a first vessel and the method can further include inserting, into the cabinet, other vessels substantially identical to the first vessel and housing other devices-under-test, connecting the other vessels to the reservoir, and recording data from the devices-under-test within the first and other vessels.

The method can further include measuring a concentration of reactive oxygen species in the vessel and dispensing peroxide into the reservoir based upon the measurement.

Each fixture includes a first part yoked to a second part so as to permit limited movement between the first and second parts. The first and second parts adapted to hold portions of the respective device-under-test that are flexibly interconnected. The method further includes pulsing pressure in the liquid in order to induce cyclic mechanical fatigue between the portions of the device-under-test.

The heating can be performed with an immersion heater whose immersion length is coated in polymer.

The cabinet can be an 18 U-or-greater size server cabinet.

DETAILED DESCRIPTION

An accelerated lifetime testing system can serve to verify long-term durability of a neural device in a short amount of time with high statistical confidence. This may be especially important before implantation into live organisms, where one is to be confident that the device will not fail during the intended implantation period.

Figure 1:
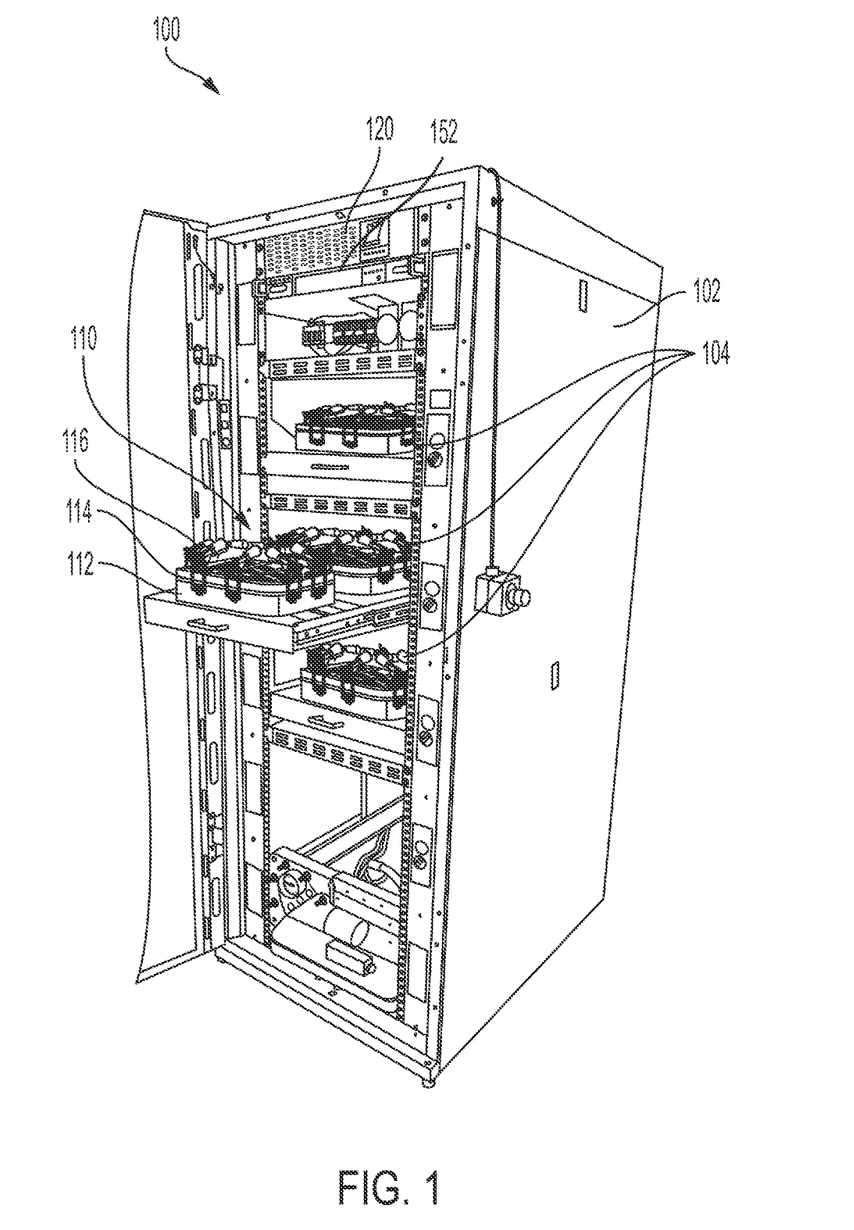
FIG. 1 illustrates an example of an accelerated testing apparatus according to some embodiments.

FIG. 1 illustrates an example of an accelerated testing apparatus 100 according to some embodiments. The accelerated testing apparatus 100 includes a cabinet 102 with multiple bays 104. The cabinet 102 may be a server rack, and in some examples may be an 18 U-or-greater size server rack. Each of the multiple bays 104 may include a shelf, which may be translatable into and at least partially out of the cabinet 102. The bays 104 can receive and store one or more vessels, such as vessel 110. Each of the vessels can be substantially identical to the vessel 110. The vessel 110 may be inserted and removed from the bays 104, which may be aided by translation of the shelf. As illustrated, each of the bays 104 of the cabinet 102 can hold two vessels, but bays in other examples may hold more or fewer vessels.

In some embodiments, the vessel 110 includes a watertight basin 112 and a radio-frequency (RF) transparent lid 114. RF transparent materials may permit RF signals to penetrate and pass through the material. Within the vessel 110 are fixtures that each anchor a device-under-test while submersed in the vessel 110. The vessel 110 may be modular, as three-dimensionally printed, such that if a design of the device-under-test is changed, an updated vessel can be quickly generated. The device-under-test may be a brain implant, such as a device with hundreds or thousands of electrodes that can be implanted into a cranium. Fixtures and devices-under-test are further described in FIGS. 3, 4, 5A, and 5B. The vessel 110 also includes a latching mechanism 116, such as a clamp or latch, to force together the lid 114 and the watertight basin 112 to hermetically seal the vessel 110.

The accelerated testing apparatus 100 can additionally include a computer server 120 operatively coupled with an antenna 152 within the cabinet for communication with each of the devices-under-test. Data, such as internal physical properties, associated with the devices-under-test can be continuously received and indexed by the computer server 120. While one computer server is shown in FIG. 1, other embodiments may include a larger number of computer servers.

The term "substantially identical" refers to items that are equal in geometry, size, and configuration such that one item may be replaced with the other item with negligible effect on form and function, or as otherwise known in the art. It may or may not include different materials depending on whether the different materials materially affect function of the item. For example, a metal may be replaced with another metal or plastic so long as the replacement plastic does not affect the primary function of the item.

Figure 2:
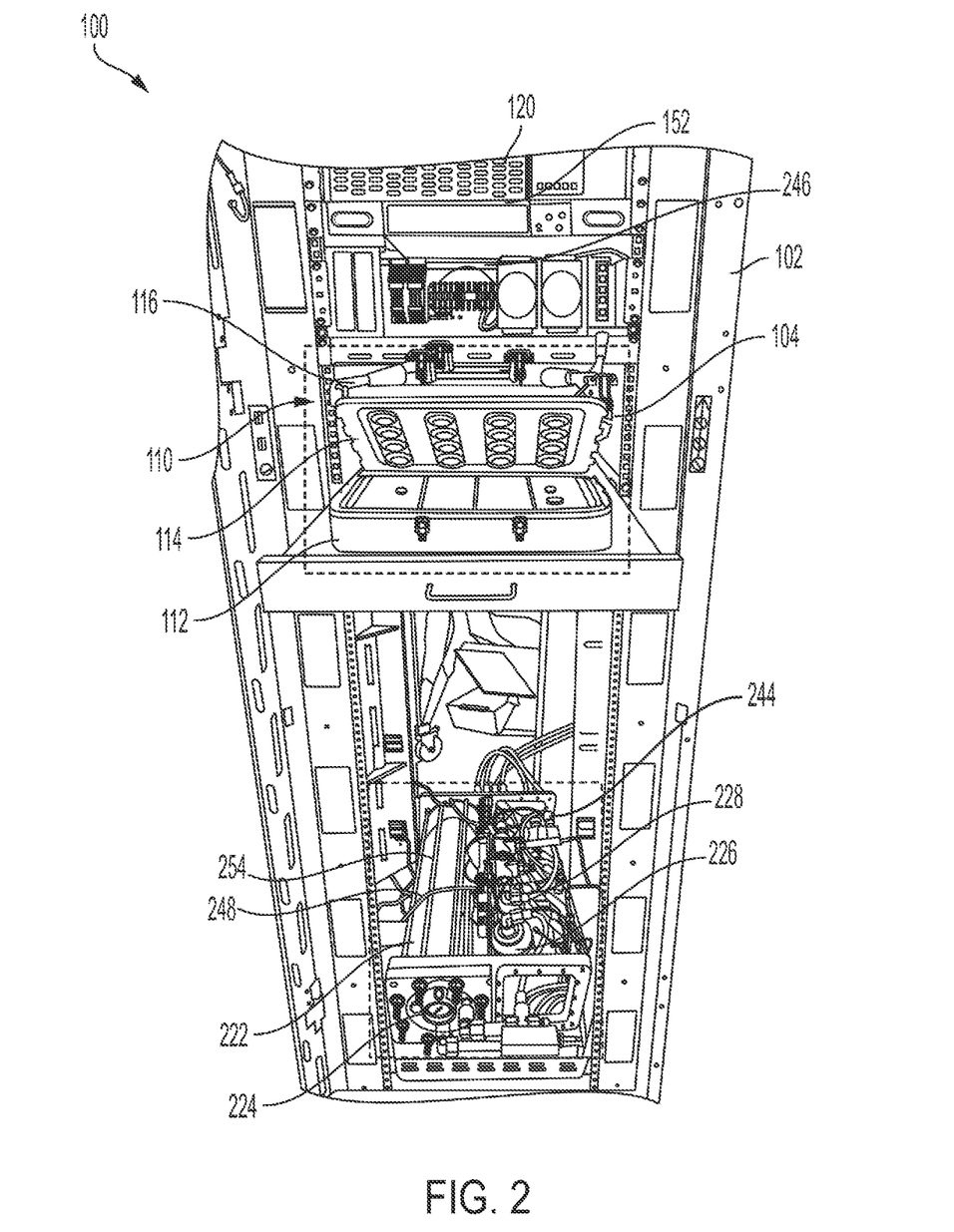
FIG. 2 is a front view of the accelerated testing apparatus of FIG. 1.

FIG. 2 is a front view of the accelerated testing apparatus 100 according to some embodiments. As illustrated, the cabinet 102 includes the bay 104, which includes the vessel 110. The RF transparent lid 14 of the vessel 110 is open, and thus not sealed to the watertight basin 112 with the latching mechanism 116. The accelerated testing apparatus 100 also includes a reservoir 222 disposed within the cabinet 102. The reservoir 222 includes a liquid with properties intended to be similar to that of cerebral spinal fluid (CSF). As such, the liquid may be considered synthetic CSF. Solvent pH, ionic strength and conductivity, and reactive oxygen species can be present in the synthetic CSF to chemically mimic the in-vivo environment. The vessel 110 can be connected to and share common liquid with the reservoir 222. In an exemplary embodiment, the vessel 110 can hold two-hundred milliliters of liquid, and the reservoir 222 can hold eight liters of liquid. A pressure sensor 224 may be disposed on an external surface of the reservoir 222. The pressure sensor 224 can measure a pressure within the reservoir 222 and the vessel 110. In some examples, the reservoir 222 and the vessel 110 are pressurized to a desired pressure, such as at least 202,650 pascals (i.e., 2 atmospheres). Additionally, in an exemplary embodiment, the pH of the liquid can be 7.4 and the ionic concentration of the liquid can be 6000 microsiemens/cm.

Other components associated with the reservoir 222 may additionally be disposed within the cabinet 102 and in proximity to the reservoir 222. The other components may include a heater 226 connected with the reservoir 222, a pump 228 for circulating the liquid between the reservoir 222 and the vessel 110, and an antenna 152 operatively connected with the computer server 120 within the cabinet 102 for communication with the devices-under-test within the vessel 110, a peroxide dispenser 244 fluidically connected with the reservoir 222, a controller 246 connected with the computer server 120, and one or more sensors 248 within the reservoir 222 for measuring pH, ionic concentration, temperature, or pressure.

The accelerated testing apparatus 100 can generate an environment similar to an in-vivo environment but with factors accelerated so as to cause the devices-under-test to fail realistically, but at an accelerated rate than in-vivo. A realistic failure mode can refer to a failure mode for the device-under-test that is capable of occurring with the device implanted into a body. For example, the pump 228 can pump the liquid from the reservoir 222 through the vessel 110. The pump can circulate a constantly-replenishing liquid, which is more similar to what occurs in a brain than heating stationary fluid that is replaced every couple of days. Additionally, the heater 226 can heat the liquid to a temperature above an average body temperature. For example, if an average body temperature is 37° C., the heater 226 may heat the liquid to 57° C., or a different elevated temperature that results in a realistic failure mode of the devices-under-test at an accelerated rate. Heating the temperature too high may result in the devices-under-test failing in an unrealistic way, therefore there may be an upper limit to the temperature that the heater heats the liquid to. The heater 226 may be an immersion heater, and metal portions 254 along an immersion length of the immersion heater can be coated in polymer (e.g., Teflon). Additionally, the synthetic CSF can include peroxide to act as a reactive oxygen species that mimics oxidative effects that occur in-vivo. The peroxide concentration can be higher than measured in-vivo levels without resulting in unrealistic degradation or failure of the devices-under test. For example, the concentration of the peroxide may be 2.5 millimolars. The addition of peroxide can also allow the temperature acceleration to be conservative to avoid an unrealistic failure mode. Pressure can be increased so that in the event of a packaging breach of the device-under-test, the effusion of moisture into the packaging is accelerated, again decreasing time to failure without causing unrealistic failure modes. The controller 246 can pulse pressure from the pump 228 to induce and exaggerate cyclic mechanical fatigue between felt portions of the device-under-test and accelerate mechanical fatigue and failure. The controller 246 can maintain the pressure within a yield stress of the material of the device-under-test to decrease time to failure without causing any non-reversible plastic deformation or another unrealistic failure mode.

In some embodiments, the computer server 120 is operatively connected with the antenna 152 that can provide wireless communication between the computer server 120 and the devices-under-test. Additionally, the peroxide sensor 248 disposed within the reservoir 222 can be connected with the computer server 120. The computer server 120 can automatically command or withhold dispensing peroxide from the peroxide dispenser 244 based upon measurements from the peroxide sensor 248. For example, if the computer server 120 determines an amount peroxide in the liquid exceeds a maximum limit, the computer server 120 can command the peroxide dispenser 244 to withhold dispensing peroxide. Alternatively, if the computer server 120 determines the amount of peroxide in the liquid is below a minimum limit, the computer server 120 can command the peroxide dispenser 244 to dispense additional peroxide.

Figure 3:
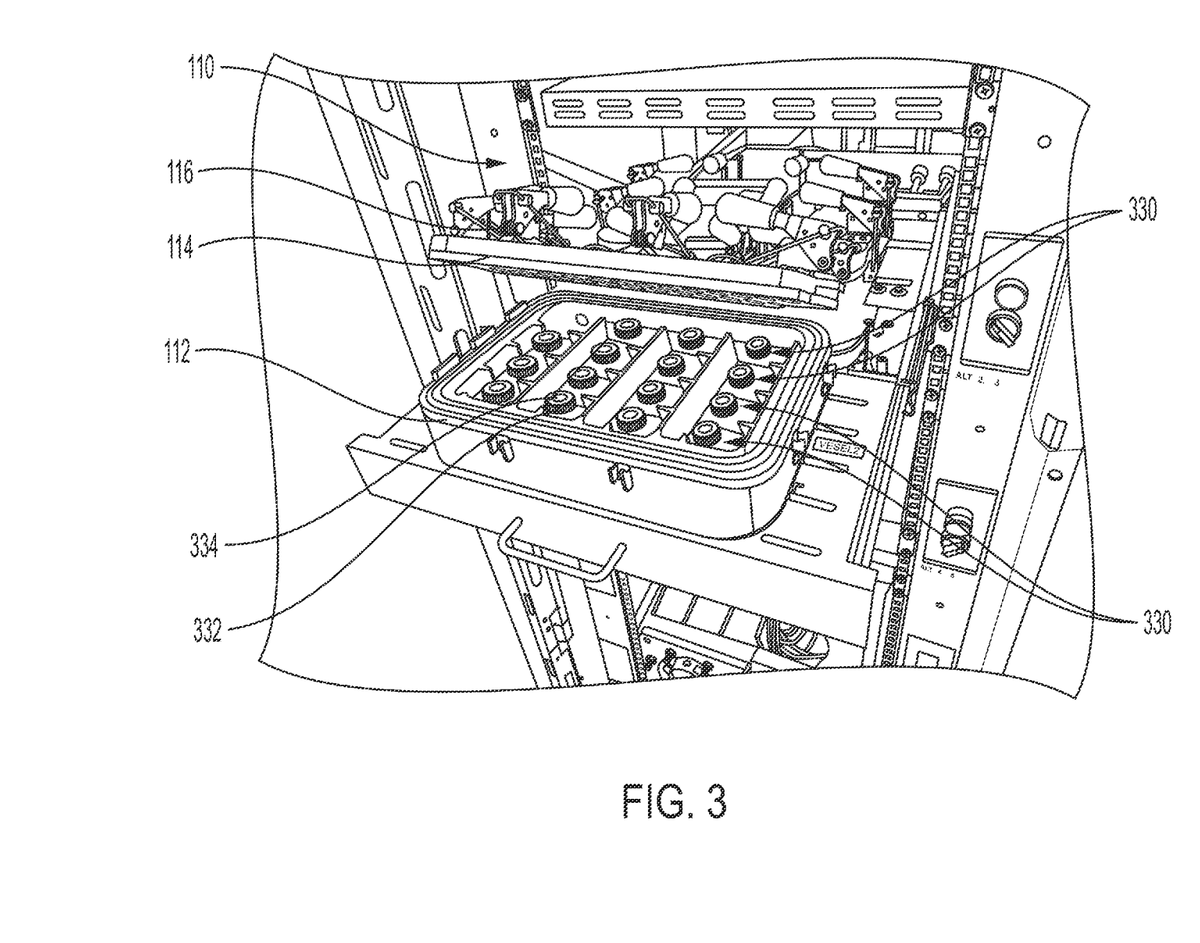
FIG. 3 illustrates an example of a vessel and fixtures of the accelerated testing apparatus of FIG. 1.

FIG. 3 illustrates an example of the vessel 110 and fixtures 330 of the accelerated testing apparatus of FIGS. 1 and 2. In an exemplary embodiment, the vessel 110 can hold sixteen fixtures. The vessel 110 includes a watertight basin 112 and a RF transparent lid 114 that can be forced together by the latching mechanism 116, which is illustrated in FIG. 3 as a lever clamp. Each of the fixtures 330 anchors a device-under-test. Additionally, the accelerated testing apparatus can include a dock 332 for a power transmission coil 334 adjacent to each of the fixtures 330. The dock 332 is illustrated as being on top of the fixture 330, and the power transmission coil 334 is illustrated as being on top of the dock 332. The power transmission coil 334 is adapted to power the respective device-under-test within the fixture 330 and can provide wireless charging for the devices-under-test.

Figure 4:
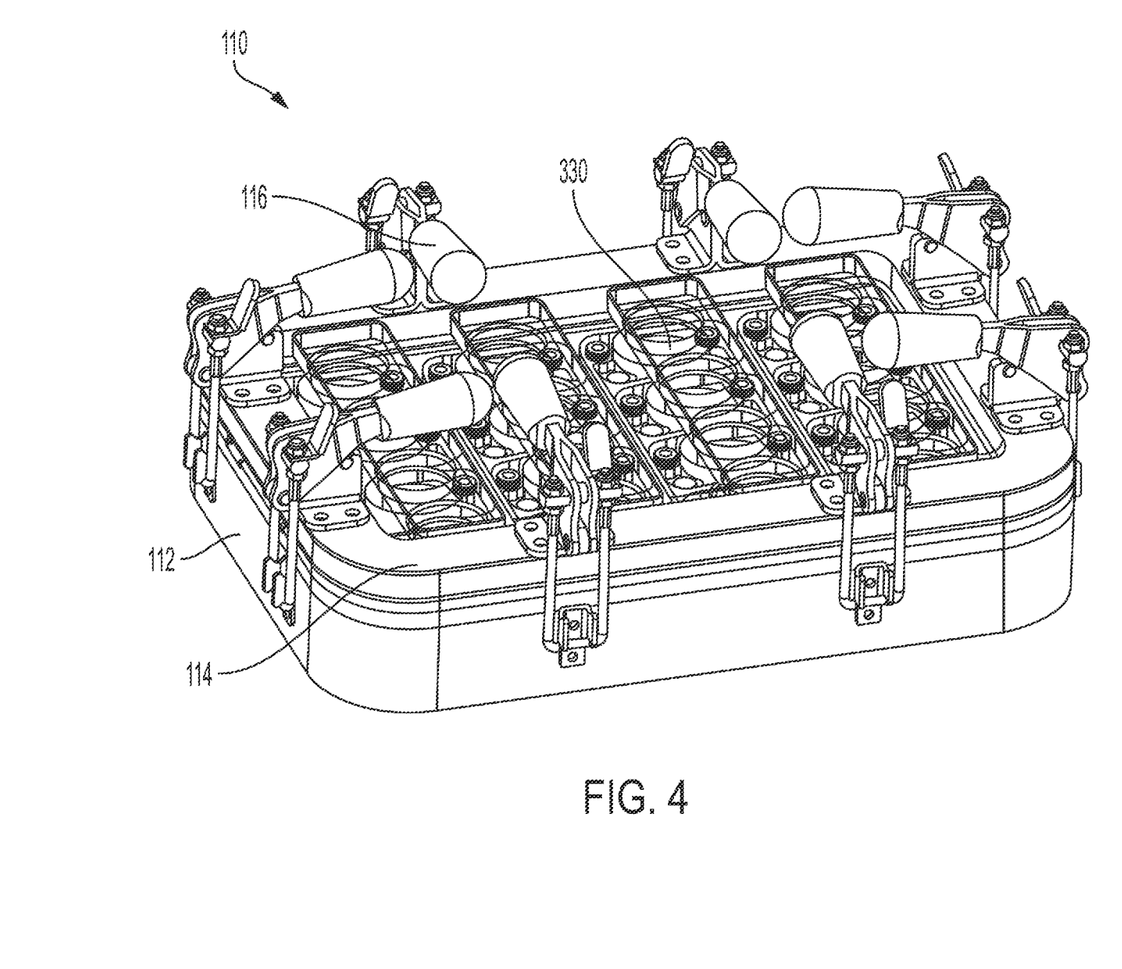
FIG. 4 illustrates a closed vessel of the accelerated testing apparatus of FIG. 1.

FIG. 4 illustrates a closed vessel 110 of the accelerated testing apparatus of FIG. 1. The RF transparent lid 114 of the vessel 110 is forced together with the latching mechanism 116 to hermetically seal the vessel 110. Similar to FIG. 3, the vessel 110 includes sixteen fixtures 330 that anchor devices-under test.

Figure 5A:
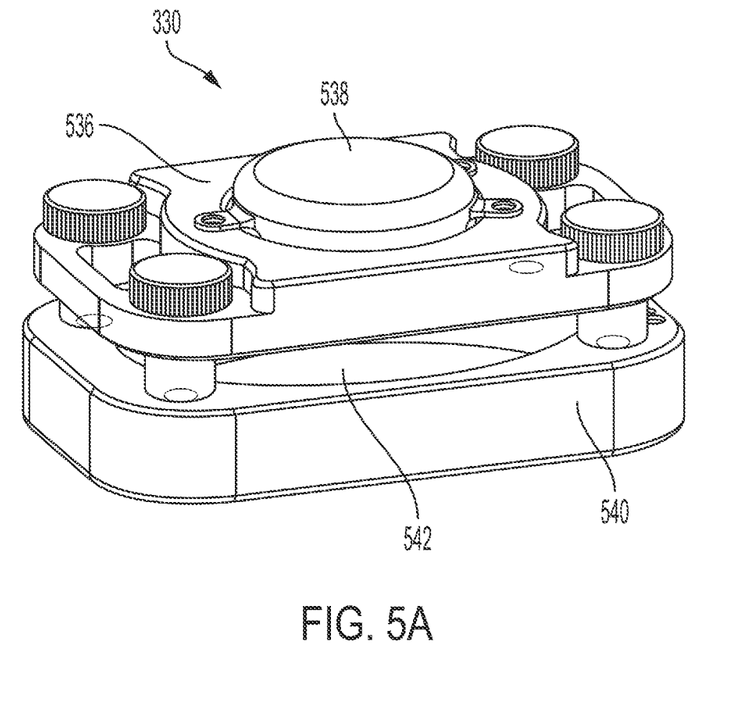
FIG. 5A shows an example of a fixture with yoked parts according to some embodiments.
Figure 5B:
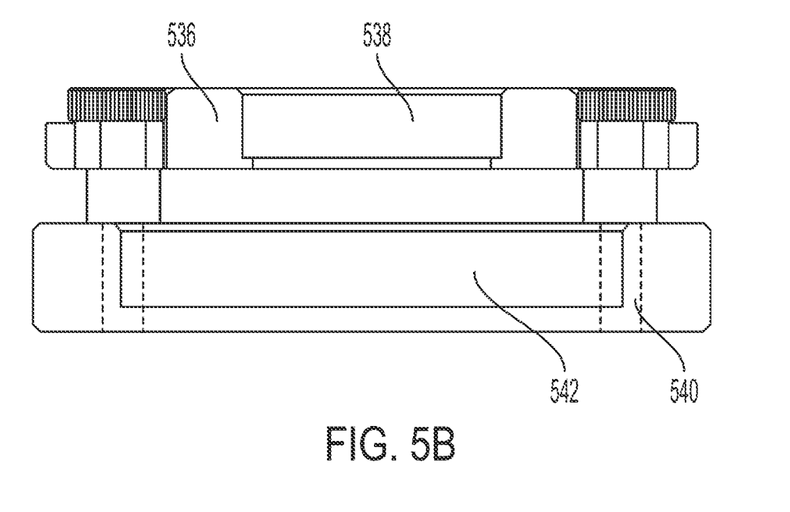
FIG. 5B is a side view of the fixture of FIG. 5A.

FIGS. 5A-5B show an example of a fixture 330 according to some embodiments. The fixture 330 includes a first part 536 yoked to a second part 540 to permit movement between the first part 536 and the second part 540. The movement between the first part 536 and the second part 540 can mimic relative motion between a brain and a cranium in-vivo. Additionally, the first part 536 and the second part 540 can be adapted to hold portions of the respective device-under-test that are flexibly interconnected. For example, the first part 536 can include a device well 538 into which a body of the device-under-test can be affixed. In addition, the second part 540 of the fixture 330 can include a simulated tissue well 542 into which electrodes from the device-under-test can be affixed. The electrodes can be sewn into a brain-like material known as conductive agarose to mimic mechanical stresses that the electrodes experience throughout implantation.

Figure 6:
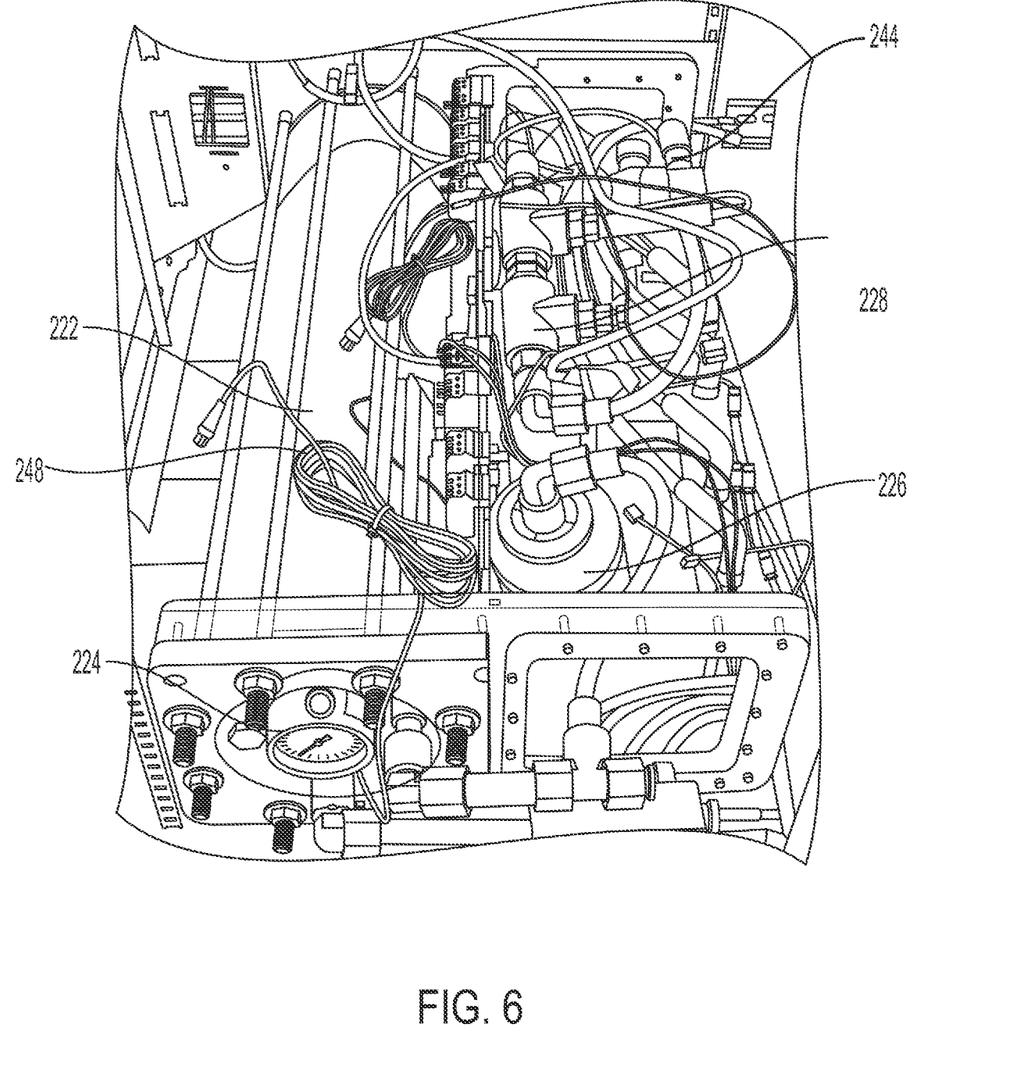
FIG. 6 illustrates a reservoir and other components of the accelerated testing apparatus of FIG. 1.

FIG. 6 illustrates a reservoir 222 and other components of the accelerated testing apparatus of FIG. 1. For example, the accelerated testing apparatus can include a sensor 224 for measuring pressure within the reservoir 222 and vessels (e.g., vessel 110) of the accelerated testing apparatus. The sensor 224 may additionally measure pH, ionic concentration, and/or temperature of the liquid within the reservoir 222. Alternatively, one or more additional sensors may measure properties of the liquid. The accelerated testing apparatus may additionally include a peroxide dispenser (e.g., peroxide dispenser 244), a peroxide sensor (e.g., sensors 248), a controller (e.g., controller 246), a pump (e.g., pump 228), a heater (e.g., heater 226), and/or an antenna (e.g., antenna 152) for performing functions as previously described. A computer server (e.g., computer server 120) can receive various measurements associated with the sensor(s) and device-under-test, so that conditions of the accelerated testing apparatus can be analyzed and failure analysis can be performed for the devices-under-test.

Figure 7:
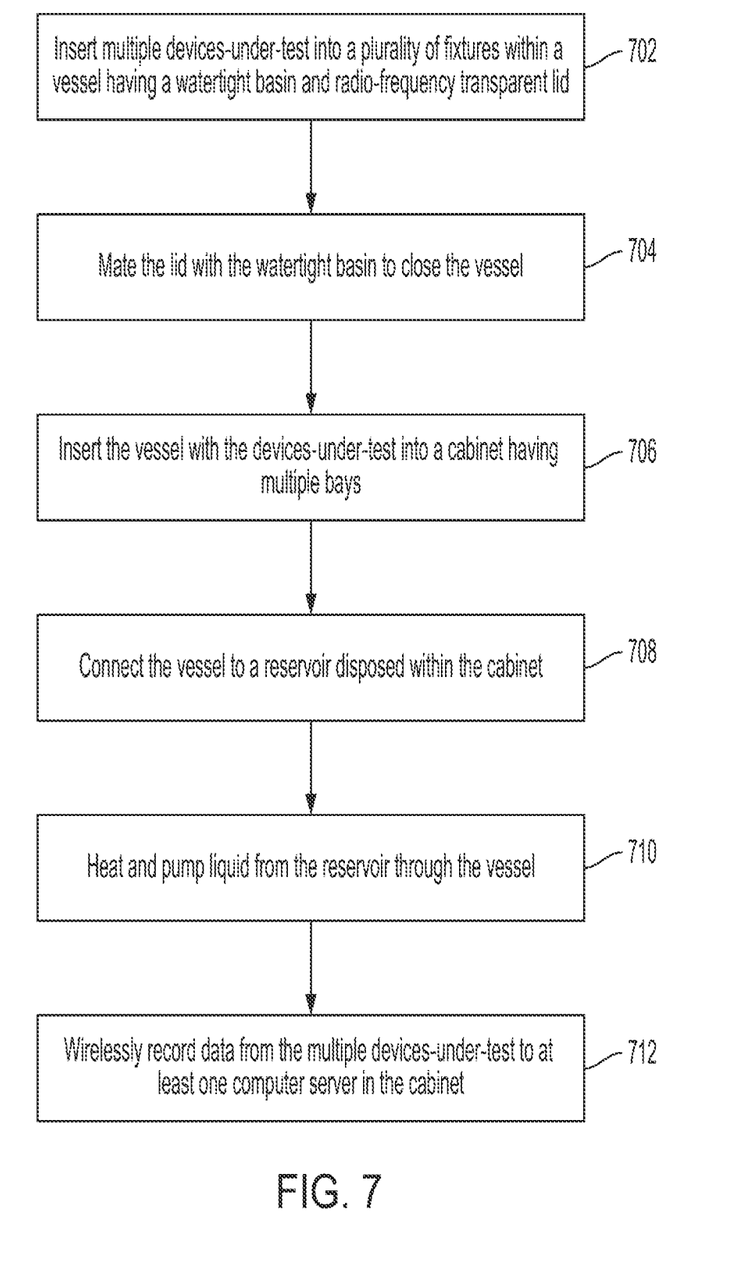
FIG. 7 is a flowchart illustrating an embodiment in accordance with the present invention.

FIG. 7 is a flowchart of a process in accordance with an embodiment. In operation 701, multiple devices-under-test are insert into a plurality of fixtures within a vessel having a watertight basin and RF transparent lid. In operation 702, the lid is mated with the watertight basin to close the vessel. In operation 703, the vessel with the devices-under-test is inserted into a cabinet having multiple bays. In operation 704, the vessel is connected to a reservoir disposed within the cabinet. In operation 705, liquid is heated and pumped from the reservoir through the vessel. In operation 706, data from the multiple devices-under-test is wirelessly recorded to at least one computer server in the cabinet.

It should be appreciated that a brain implant or other system and a respective control system for the brain implant can have one or more microprocessors/processing devices that can further be a component of the overall apparatuses. The control systems are generally proximate to their respective devices, in electronic communication (wired or wireless) and can also include a display interface and/or operational controls configured to be handled by a user to monitor the respective systems, to change configurations of the respective systems, and to operate, directly guide, or set programmed instructions for the respective systems, and sub-portions thereof. Such processing devices can be communicatively coupled to a non-volatile memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C #, Java, Python, Perl, JavaScript, etc.

While the above description describes various embodiments of the invention and the best mode contemplated, regardless how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

In some embodiments, the systems and methods of the present disclosure can be used in connection with neurosurgical techniques. However, one skilled in the art would recognize that neurosurgical techniques are a non-limiting application, and the systems and methods of the present disclosure can be used in connection with any biological tissue. Biological tissue can include, but is not limited to, the brain, muscle, liver, pancreas, spleen, kidney, bladder, intestine, heart, stomach, skin, colon, and the like.

The systems and methods of the present disclosure can be used on any suitable multicellular organism including, but not limited to, invertebrates, vertebrates, fish, bird, mammals, rodents (e.g., mice, rats), ungulates, cows, sheep, pigs, horses, non-human primates, and humans. Moreover, biological tissue can be ex vivo (e.g., tissue explant), or in vivo (e.g., the method is a surgical procedure performed on a patient).

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples; alternative implementations may employ differing values or ranges, and can accommodate various increments and gradients of values within and at the boundaries of such ranges.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

What is claimed is:

1. An accelerated testing apparatus for implants, the apparatus comprising:
    a cabinet having multiple bays;
    a vessel insertable and removable from any of the multiple bays, the vessel comprising:
        a watertight basin;
        a radio-frequency (RF) transparent lid configured to mate with the basin; and
        a plurality of fixtures within the vessel, each fixture adapted to anchor a device-under-test while submersed within the vessel;
    a reservoir disposed within the cabinet;
    a heater connected with the reservoir;
    a pump configured to circulate liquid between the reservoir and the vessel;
    a controller configured to pulse pressure from the pump in order to induce cyclic mechanical fatigue between the portions of the device-under-test, wherein the controller is connected to the heater and to at least one computer server;
    an antenna within the cabinet for communication with the device-under-test and wherein the at least one computer server is operatively connected with the antenna.

2. The apparatus of claim 1 wherein the vessel is a first vessel, the apparatus further comprising:
    other vessels substantially identical to the first vessel, wherein the first and other vessels are installed in the cabinet and connected to and share common liquid with the reservoir,
    wherein the at least one computer server is configured to index multiple devices-under-test within the vessels and regardless of position within the cabinet and record data from the multiple devices-under-test.

3. The apparatus of claim 1 further comprising:
a peroxide dispenser fluidically connected with the reservoir.

4. The apparatus of claim 3 further comprising:
a peroxide sensor disposed within the reservoir and connected with the at least one computer server via the controller, the computer server configured to command or withhold dispensing of peroxide from the peroxide dispenser based upon measurements from the peroxide sensor.

5. The apparatus of claim 1 wherein each fixture comprises a first part yoked to a second part so as to permit limited movement between the first and second parts, the first and second parts adapted to hold portions of the respective device-under-test that are flexibly interconnected.

6. The apparatus of claim 5 wherein the second part of the fixture includes a simulated tissue well into which electrodes from the device-under-test can be affixed.

7. The apparatus of claim 1 wherein the heater is an immersion heater.

8. The apparatus of claim 7 wherein metal portions along an immersion length of the immersion heater are coated in polymer.

9. The apparatus of claim 1 further comprising:
a clamp or latch configured to force together the lid and watertight basin to hermetically seal the vessel,
wherein the vessel and the reservoir are configured to be pressurized to at least 202,650 pascals (2 atmospheres).

10. The apparatus of claim 1 further comprising:
a dock for a power transmission coil adjacent to each fixture, wherein the power transmission coil is adapted to power the respective device-under-test.

11. The apparatus of claim 1 further comprising:
a sensor connected with the reservoir and configured to measure pH, ionic concentration, temperature, or pressure.

12. The apparatus of claim 1 wherein the cabinet comprises an 18 U-or-greater size server cabinet.

13. A method for accelerated testing implants, the method comprising:
inserting multiple devices-under-test into a plurality of fixtures within a vessel having a watertight basin and radio-frequency (RF) transparent lid;
mating the lid with the watertight basin to close the vessel;
inserting the vessel with the devices-under-test into a cabinet having multiple bays, the vessel being insertable and removable from any of the multiple bays;
connecting the vessel to a reservoir disposed within the cabinet;
heating and pumping liquid from the reservoir through the vessel, wherein the heating and pumping is controlled by a controller and wherein the controller is connected to at least one computer server;
pulsing pressure in the liquid in order to induce cyclic mechanical fatigue between the portions of the device-under-test; and
wirelessly recording data from the multiple devices under test to the at least one computer server in the cabinet, thereby accelerating the testing of the implants by determining an appropriate implantation period for the implants based on the cyclic mechanical fatigue data.

14. The method of claim 13 wherein the vessel is a first vessel, the method further comprising:
inserting, into the cabinet, other vessels substantially identical to the first vessel and housing other devices-under-test;
connecting the other vessels to the reservoir; and
recording data from the devices-under-test within the first and other vessels.

15. The method of claim 13 further comprising:
measuring a concentration of reactive oxygen species in the vessel; and
dispensing peroxide into the reservoir based upon the measurement.

16. The method of claim 13 wherein each fixture comprises a first part yoked to a second part so as to permit limited movement between the first and second parts, the first and second parts adapted to hold portions of the respective device-under-test that are flexibly interconnected.

17. The method of claim 13 wherein the heating is performed with an immersion heater whose immersion length is coated in polymer.

18. The method of claim 13 wherein the cabinet comprises an 18 U-or-greater size server cabinet.

* * * * *